United States Patent [19]

Paparizos et al.

[11] Patent Number: 4,714,695
[45] Date of Patent: Dec. 22, 1987

[54] METHOD FOR THE PREPARATION OF HIGH ACTIVITY PALLADIUM BASED CATALYSTS

[75] Inventors: Christos Paparizos, Willowick; Wilfrid G. Shaw, Lyndhurst; James L. Callahan, Wooster, all of Ohio

[73] Assignee: The Standard Oil Company, Cleveland, Ohio

[21] Appl. No.: 852,733

[22] Filed: Apr. 16, 1986

Related U.S. Application Data

[63] Continuation of Ser. No. 724,535, Apr. 18, 1985, Pat. No. 4,623,635.

[51] Int. Cl.$^4$ .................. B01J 23/42; B01J 31/00; B01J 27/24; B01J 27/057
[52] U.S. Cl. ................... 502/339; 502/170; 502/200; 502/215; 502/230; 502/241; 502/243; 502/246; 502/262; 502/324; 502/527
[58] Field of Search .............. 502/170, 200, 215, 230, 502/241, 243, 246, 262, 324, 339, 527

[56] References Cited

U.S. PATENT DOCUMENTS

| | | | |
|---|---|---|---|
| 2,662,861 | 12/1953 | Ribett et al. | 252/455 |
| 2,802,889 | 8/1957 | Krevel et al. | 260/677 |
| 3,584,065 | 6/1971 | Oshima | 260/654 |
| 3,772,383 | 11/1973 | Kominami et al. | 260/479 |
| 3,959,352 | 5/1976 | Onoda et al. | 252/430 |
| 3,959,354 | 5/1976 | Onoda et al. | 260/621 G |
| 4,016,200 | 4/1977 | Onoda et al. | 260/488 |
| 4,033,999 | 7/1977 | Onoda et al. | 252/430 |
| 4,093,559 | 6/1978 | Fernholz et al. | 252/443 |
| 4,107,204 | 8/1978 | Murib | 260/530 |
| 4,354,961 | 10/1982 | Kamiyama et al. | 252/439 |
| 4,499,298 | 2/1985 | Scheben et al. | 502/215 |
| 4,520,125 | 5/1985 | Baer et al. | 502/170 |

FOREIGN PATENT DOCUMENTS

| | | |
|---|---|---|
| 56-53625 | 10/1979 | Japan . |
| 56-71040 | 11/1979 | Japan . |
| 56-90038 | 12/1979 | Japan . |
| 56-122370 | 3/1980 | Japan . |
| 57-50545 | 9/1980 | Japan . |
| 5748938 | 9/1980 | Japan . |
| 1433168 | 4/1976 | United Kingdom . |
| 2051056 | 6/1983 | United Kingdom . |

Primary Examiner—Andrew H. Metz
Assistant Examiner—William G. Wright
Attorney, Agent, or Firm—M. F. Esposito; J. E. Miller; L. W. Evans

[57] ABSTRACT

A method for the preparation of a high activity palladium metal based catalyst having the formula

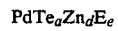
$$PdTe_aZn_dE_e$$

where
E is one or more metals from the group IIA, IVA, VA, IB, VIIB or VIII; and
a, d and e are from about 0 to 3, with the proviso that at least d or e$\neq$0.

The method comprises the step of forming an aqueous solution of a palladium compound, adding to the solution a powder of a reducing metal more electropositive than palladium and reducing the palladium to its metallic state on the surface of the reducing metal and, separating the resulting catalyst from the solution. Catalysts prepared according to this method are useful for producing esters from aldehydes and alcohols and provide greater conversions to the ester than catalysts prepared by previous processes.

6 Claims, No Drawings

METHOD FOR THE PREPARATION OF HIGH ACTIVITY PALLADIUM BASED CATALYSTS

This application is a continuation of application Ser. No. 724,535, filed Apr. 18, 1985, U.S. Pat. No. 4,623,635.

TECHNICAL FIELD

Catalysts comprising palladium metal and various alloys thereof have recognized utility in several areas of petrochemical processing. An area of particular importance and which relates to the present invention is the use of palladium based catalysts for the selective direct oxidation and esterification of unsaturated aldehydes such as methacrolein in the presence of an alcohol to the corresponding methacrylic acid ester. Catalysis with palladium in combination with small amounts of promoter elements such as tellurium on the surface of more electropositive metals is a process of economic interest. The present invention sets forth a method for the preparation of a palladium based catalyst having a high activity for the more efficient conversion of, for example, methacrolein to a methacrylic acid ester.

BACKGROUND ART

At least one method for the preparation of catalysts for the oxidation and esterification of unsaturated aldehydes to unsaturated acid esters is known in the art. This method involves the preparation of palladium catalysts suitable for methacrolein esterification and uses formaldehyde/potassium hydroxide solutions to reduce a mixture of salts of metals. However, this method of preparation is expensive and requires extensive washing of the obtained alloys prior to the rather difficult removal of potassium hydroxide from the catalyst.

DISCLOSURE OF THE INVENTION

In general, the method of the present invention for the preparation of a palladium metal based catalyst having the formula

$PdTe_aZn_dE_e$ where
E is one or more metals from group IIA, IIIA, IVA, VA, IB, VIIB or VIII; and
a, d and e are from about 0 to 3, with the proviso that at least d or e≠0, comprises the steps of forming an aqueous solution of a palladium compound, adding to the solution a powder of a reducing metal more electropositive than palladium and reducing the palladium to its metallic state on the surface of the reducing metal and, separating the resulting catalyst from the solution. Elements other than Te or Zn such as appear in group E can optionally be added as catalyst promoters during the step of forming the solution of a palladium compound.

PREFERRED MODE FOR CARRYING OUT THE INVENTION

The catalyst of the present invention is a palladium based catalyst which can optionally be provided with one or more metallic promoters. Suitable palladium compounds selected for preparation of the catalyst include most inorganic salts such as $PdCl_2$, $Pd(NO_3)_2$, $PdBr_2$, $PdI_2$ and the like as well as salts formed with carboxylic acids such as $Pd(C_2H_3O_2)_2$. Regarding the promoter metals, elements such as tellurium are preferred although other metals can also be employed.

Actual preparation of the catalyst involves dissolving a palladium compound and optionally one or more compounds of metallic promoters in water. The palladium compound and optional promoter elements are preferably salts and all components are preferably dissolved in water so that the final solution consists essentially of a mixture of palladium compound and the dissolved and optional promoter-containing compound(s).

In the practice of the present invention, the palladium is present in the final solution at a concentration of from 0.01 to 20 percent by weight, preferably from 0.1 to 2. Concentration of the one or more promoter compounds, where present, in the final solution is from 0.01 to about 5 percent by weight. The amount of tellurium or other promoter element present in the catalyst ranges from about 0.01 to 3 parts per part of palladium metal.

Added to the final solution, preferably with stirring, is a powder of a reducing metal which is more electropositive than palladium. This reducing metal is added in a quantity in excess of that required to reduce the palladium present to palladium metal. Where a promoter compound(s) is present, it is also preferred that a sufficient amount of reducing metal be employed to reduce the metal ion of the promoter compound(s) to the metallic state. The reducing metal is also preferably more electropositive than the promoter metal(s). Particle size of the reducing metal can range from about 10 to 80 mesh although particle sizes are not necessarily excluded.

As noted hereinabove, the subject catalyst can be optionally promoted by an E group element where E comprises one or more metals selected from the group consisting of groups IIA, IIIA, IVA, VA, IB, VIIB or VIII. These group designations are from the Deming Periodic Table whereing group IIIA includes the elements B, Al, Ga, In, Tl; Group IVA includes the elements C, Si, Ge, Sn, Pb; Group VA includes the elements N, P, As, Sb, Bi; and Group VIIB includes the elements Mn, Tc, Re, The preferred E group promotor elements include Al, Pb, Sn, Sb, Bi, Cu, Ag, Au and Fe. The preferred reducing metal is Zn which is also an optional promoter metal. Where d=0 and Zn is not present, one of the group E elements can be employed as the reducing metal so long as it is more electropositive than Pd and any of the promoter elements from group E or Te that are selected, as noted hereinabove. Other preferred reducing metals include Cu, Pb, Fe and Mg.

The amount of the reducing metal employed can be partially determined stoichiometrically, based upon the amount required to reduce the palladium and to generate the promoter metal. The reducing metal must also be present in the catalyst generally in an amount ranging from about 0.1 to 3 parts per part of palladium metal.

During catalyst preparation, the components are mixed together at a temperature ranging from about 20° to about 100° C. for a period of time of from about 0.01 to about 2 hours.

In the examples which follow, three different catalyst compositions were prepared either by the metal displacement technique of the present invention or, for comparison, by known chemical reduction with formaldehyde/potassium hydroxide. Table I summarizes the data obtained when these catalysts were used to convert mixtures of methanol and methacrolein to methyl methacrylate. Runs 1 and 2 employed tellurium promoted catalysts at room temperature; runs 3 and 4 employed unpromoted catalysts at room temperature and runs 5 and 6 employed unpromoted catalysts at 50° C.

Although the preparation of esters utilizing the catalysts disclosed herein does not constitute a part of the present invention, the conversion is employed to demonstrate the novelty in the method of catalyst preparation inasmuch as catalysts prepared according to the novel method show dramatic increases in the single pass yield of ester.

The conversion reaction can be conducted in a closed reaction vessel by combining the catalyst and reactants, alcohol and aldehyde, together and mixing for a period of time as has been exemplified hereinbelow. Alternatively, as will be appreciated by those skilled in the art, the reaction could also be conducted in either a fixed-bed or fluid-bed reactor at temperatures of from about 20° C. to about 100° C. and pressures of about atmospheric to about 10 atmospheres. The catalyst can be in supported or unsupported form; suitable support materials including silica, alumina, boron-phosphate, titania, zirconia and the like and preferably Alundum as well as mixtures thereof. Alundum is a registered trademark of the Norton Co., Metals Division, for fused-alumina refractory materials. The catalyst can have any of the conventional fixed-bed forms such as coated, tablet, pellet, extruded, spherical, or fluid-bed forms such as microspherical or other forms known in the art.

It is also possible for the reducing metal to form the support for the catalyst where a support is desired. In this instance significantly larger amounts of the reducing metal will be employed depending upon the surface area of catalyst that is to be exposed in any given reactor. Nevertheless, it is understood that the catalyst composition will comprise up to about 3 parts of the reducing metal per part of palladium while much larger amounts are present as the support.

All of the conversions to esters were conducted in the following manner. The catalyst (0.15 g) was placed in a 7 ounce (207 ml) beverage bottle which was sealed and flushed with oxygen for 15 minutes. Next, methanol (about 2 g) and methacrolein (about 0.2 g) were injected. The pop bottle was placed in a shaker for 16 hours after which time the mixture was analyzed. Product analysis was performed in a Hewlett-Packard Model 5710A gas chromatograph fitted with a flame ionization detector and a SP 1200 column.

As stated hereinabove, in order to evaluate the effectiveness of the catalyst prepared according to the method of the present invention, the percent per single pass yield or percent per pass conversion was calculated as follows:

$$\text{Percent Single Pass Yield} = \frac{\text{Moles of ester recovered}}{\text{Moles of methacrolein fed}} \times 100$$

EXAMPLE 1

$Pd_1Zn_1Te_{0.2}$ (metal displacement). Palladium chloride (1.77 g) was dissolved in 400 cc of water at 70° C. with stirring. To this solution a suspension of $TeO_2$ in HCl was added, (0.32 g) of $TeO_2$ in concentrated (about 12N) HCl. The temperature was allowed to raise while the mixture was stirred and then zinc metal (1.44 g) was added. The reaction was allowed to proceed at 70° C. with stirring for 1 hour and then the mixture was filtered, washed with 500 cc of water and dried over night at 110° to 120° C.

EXAMPLE 2

$Pd_1Zn_1Te_{0.2}$ (Reduction with $CH_2O$/KOH). Palladium chloride (0.886 g) and $TeO_2$ (0.159 g) were placed in a 300 cc beaker, to which was added 50 cc diluted (0.5 N) HCl. The suspension was heated to 60° C. for 30 minutes after which zinc nitrate (1.49 g in 20 cc of water) was added. The temperature was maintained at 60° C. while the reactants were stirred for 15 minutes, then 1.0 cc of formalin was added, and the solution was pH adjusted with KOH solution to a pH of about 8. A black precipitant was formed which was stirred before filtration. The precipitant was washed with 1.0 liter of water and dried in the oven at 110° to 120° C. over night.

EXAMPLE 3

$Pd_1Zn_1$ (metal displacement). This catalyst was prepared utilizing the same procedure and ingredients as Example 1, except that no promoter salt ($TeO_2$) was employed.

EXAMPLE 4

(Comparative)

$Pd_1Zn_1$ (reduction with $CH_2O$/KOH). This catalyst was prepared by the same procedure using the same ingredients as in Example 2, except that no promoter salt ($TeO_2$) was employed.

EXAMPLES 5 and 6

These were prepared substantially as Examples 3 and 4, respectively, except that 2.16 g of zinc nitrate was employed to provide a catalyst having the formula $Pd_1Zn_2$, as before.

TABLE I

| Ex. No. | Catalyst Composition | Preparation Method | Per Pass Conversion to MMA | Reaction Temp (°C.) |
|---|---|---|---|---|
| 1 | $Pd_1Zn_1Te_{0.2}$ | Metal displacement | 52.6 | Room Temp |
| 2 | $Pd_1Zn_1Te_{0.2}$ | Reduction with $CH_2O$/KOH | 15.0 | Room Temp |
| 3 | $Pd_1Zn_1$ | Metal displacement | 38.2 | Room Temp |
| 4 | $Pd_1Zn_1$ | Reduction with $CH_2O$/KOH | 29.7 | Room Temp |
| 5 | $Pd_1Zn_2$ | Metal displacement | 51.9 | 50° |
| 6 | $Pd_1Zn_2$ | Reduction with $CH_2O$/KOH | 41.0 | 50° |

From the results appearing in Table I, it is clear that the intermetallic catalyst prepared by the metal displacement technique exhibited better catalytic activity (Runs 1, 3 and 5) than where chemical reduction was employed (Runs 2, 4 and 6). Run 1 provided the highest per pass conversion to the ester, employing a promoted catalyst. Run 3, did not provide as high a conversion although it was better than its comparative, Run 4. These were run at room temperature and by reviewing Run 5, conducted at 50° C., it can be seen that raising the temperature this small amount resulted in a per pass conversion essentially as high as Run 1, where a promoter was employed. In each instance, catalysts prepared according to the process of the present invention provided a greater amount of ester than their chemically reduced counterparts.

Based upon the enhanced yields of methyl methacrylate that have been obtained when a palladium based catalyst has been prepared according to the process of the present invention as set forth herein, it should be apparent that the catalysts produced by this process have greater activity. It is to be understood that the preparation disclosed herein is applicable, in general, to palladium catalysts which, as stated hereinabove, can include tellurium and/or possibly zinc and/or other metals from group E as promoters. Presence or absence of these additional promoters will not affect our unique method of preparation set forth herein.

It should be apparent to those skilled in the art that our invention is operable on palladium based catalysts having certain ratios of reducing metal to palladium and it is operable when certain promoters, temperatures and reducing metals, as employed, are varied. It is to be understood that these variables fall within the scope of the claimed invention and that it is not to be limited by the examples which are representative and demonstrate operability; and furthermore, it is believed that the selection of specific reducing metals, promoters and reaction conditions can be determined without departing from the spirit of the invention herein disclosed and described, and that the scope of the invention includes all modifications including equivalents and variations falling within the scope of the attached claims.

We claim:

1. A palladium metal based catalyst having the formula $$PdTe_a Zn_d E_e$$

where
- E is one or more metals selected from the group consisting of groups IIA, IIIA, IVA, VA, IB, VIIB or VIII;
- a, d and e are from about 0 to 3 with the proviso that at least d or e≠0, and
- Te, Zn and E are promoter elements, prepared by the steps of:
- forming an aqueous solution of a palladium compound;
- adding to said solution a powder of a reducing metal selected from the group consisting of Zn and said E group promoter metals, said metal being more electropositive than palladium, in an amount sufficient to reduce all of the palladium in said palladium compound to palladium metal;
- reducing the palladium to its metallic state on the surface of said reducing metal; and
- separating the resulting catalyst from said solution.

2. A catalyst, as set forth in claim 1, with the further proviso that if d=0, then said reducing metal selected must be more electropositive than both Pd and any of said E elements present as promoters.

3. A catalyst, as set forth in claim 2, wherein said catalyst is supported.

4. A catalyst, as set forth in claim 3, wherein said reducing metal also forms said support.

5. A catalyst, as set forth in claim 2, wherein said reducing metal is Zn and said promoter element is Te.

6. A catalyst, as set forth in claim 2, wherein said reducing metal is added in an amount sufficient to reduce all palladium in said palladium compound and any of said promoter elements to their respective metallic states.

* * * * *